US008876822B2

(12) United States Patent
Fagan et al.

(10) Patent No.: US 8,876,822 B2
(45) Date of Patent: Nov. 4, 2014

(54) INTRAMEDULLARY NAIL SYSTEM WITH TANG FIXATION AFTER LOCK SCREW PLACEMENT

(71) Applicant: Orthopedic Designs North American, Inc., Tampa, FL (US)

(72) Inventors: Lance Fagan, Tampa, FL (US); Luis Vega, Tampa, FL (US)

( * ) Notice: Subject to any disclaimer, the term of this patent is extended or adjusted under 35 U.S.C. 154(b) by 0 days.

(21) Appl. No.: 13/713,560

(22) Filed: Dec. 13, 2012

(65) Prior Publication Data
US 2013/0274747 A1 Oct. 17, 2013

Related U.S. Application Data

(63) Continuation-in-part of application No. 13/445,954, filed on Apr. 13, 2012, now Pat. No. 8,491,854.

(51) Int. Cl.
*A61B 17/72* (2006.01)
(52) U.S. Cl.
CPC ......... *A61B 17/7266* (2013.01); *A61B 17/7225* (2013.01)
USPC .......................................................... 606/64
(58) Field of Classification Search
USPC .................................................... 606/62–68
See application file for complete search history.

(56) References Cited

U.S. PATENT DOCUMENTS

| 2,998,007 | A | * | 8/1961 | Herzog | ............................ 606/63 |
|---|---|---|---|---|---|
| 3,986,504 | A | | 10/1976 | Avila | |
| 5,645,589 | A | | 7/1997 | Li | |
| 5,702,215 | A | | 12/1997 | Li | |
| 5,976,139 | A | | 11/1999 | Bramlet | |
| 6,077,264 | A | | 6/2000 | Chemello | |
| 6,183,474 | B1 | | 2/2001 | Bramlet et al. | |
| 6,443,954 | B1 | | 9/2002 | Bramlet et al. | |
| 6,447,546 | B1 | | 9/2002 | Bramlet et al. | |
| 6,488,684 | B2 | | 12/2002 | Sterghos et al. | |
| 6,554,833 | B2 | | 4/2003 | Levy et al. | |
| 6,575,973 | B1 | | 6/2003 | Shekalim | |
| 6,648,889 | B2 | | 11/2003 | Bramlet et al. | |
| 6,695,844 | B2 | | 2/2004 | Bramlet et al. | |
| 2006/0229617 | A1 | | 10/2006 | Meller et al. | |
| 2008/0161805 | A1 | | 7/2008 | Saravia et al. | |

* cited by examiner

*Primary Examiner* — Pedro Philogene
*Assistant Examiner* — David Comstock
(74) *Attorney, Agent, or Firm* — Larson & Larson, P.A.; Frank Liebenow; Justin P. Miller

(57) ABSTRACT

The disclosed device solves the problem of fixation of a fractured humerus, or other long bone, by allowing a surgeon to first fix the proximal end of the implant and set the fracture, followed by fixation of the distal end without the use of screws.

16 Claims, 17 Drawing Sheets

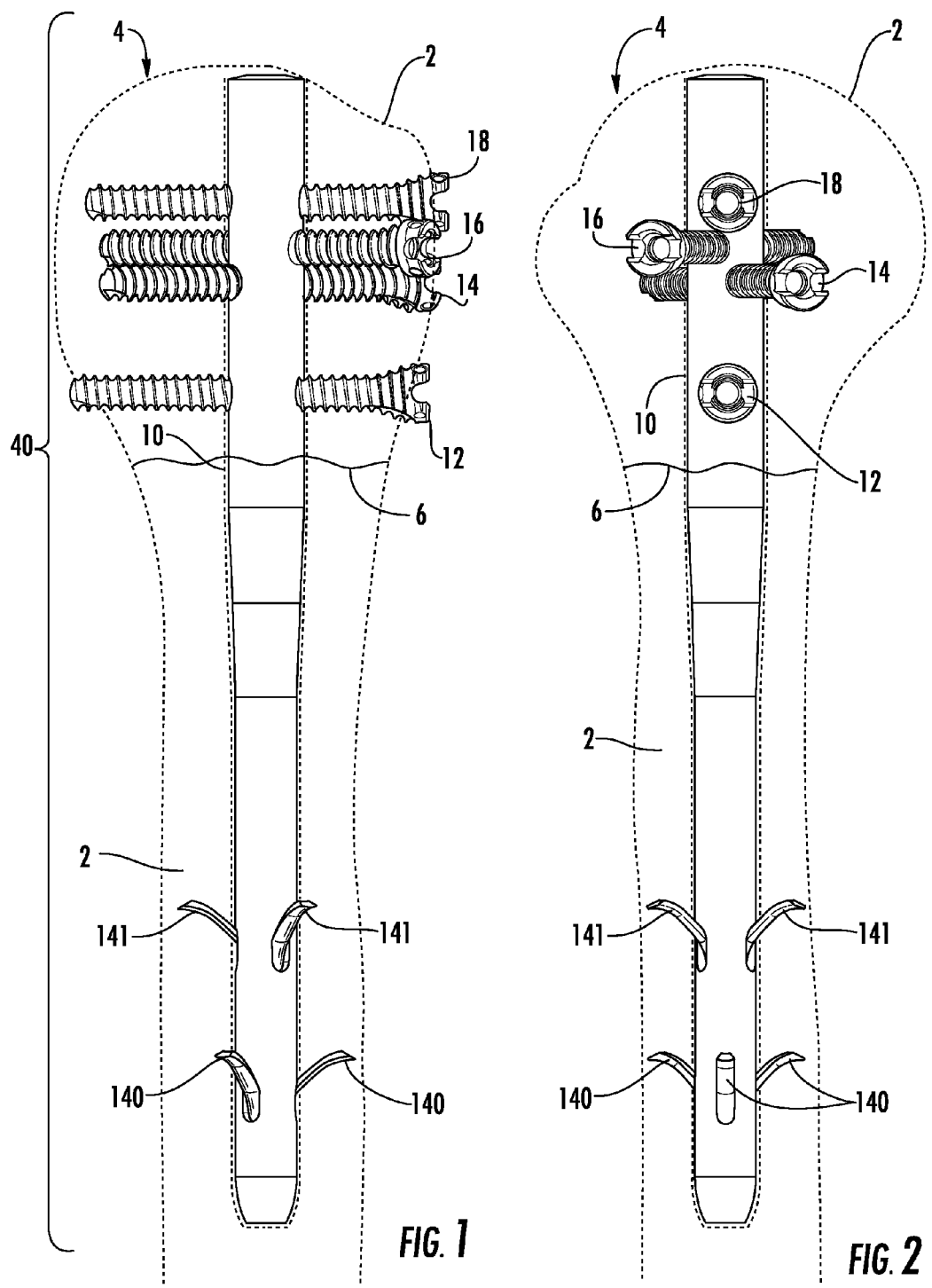

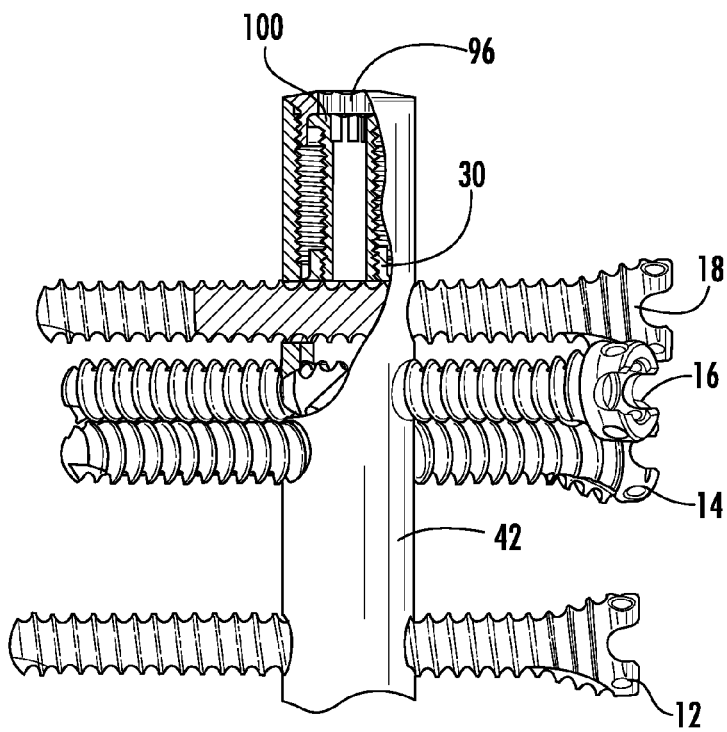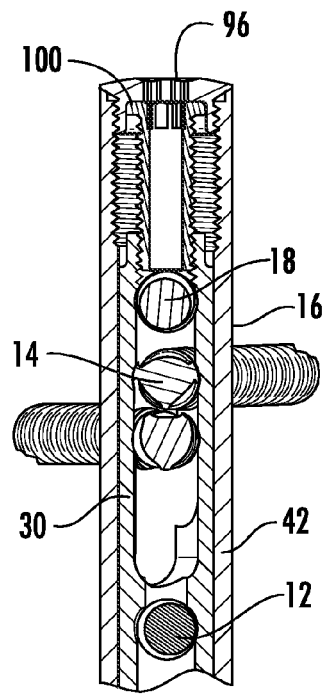
FIG. 5          FIG. 6
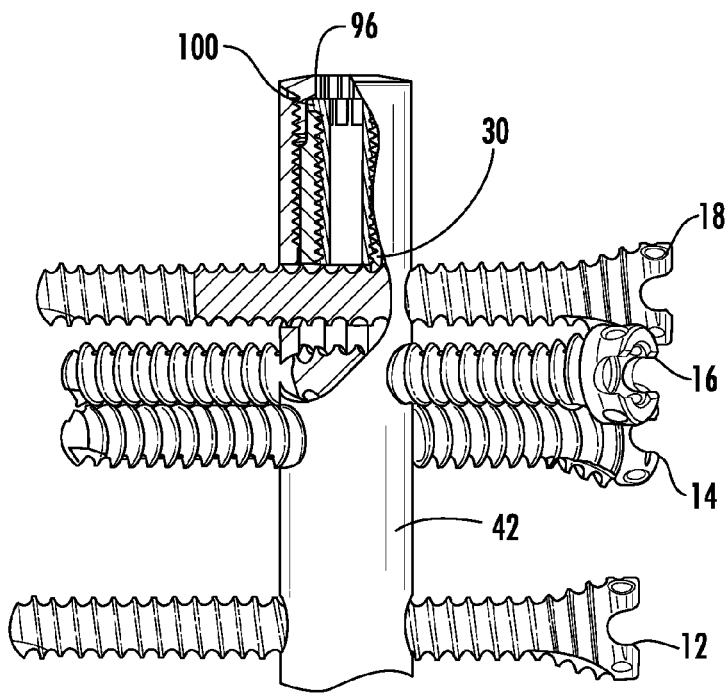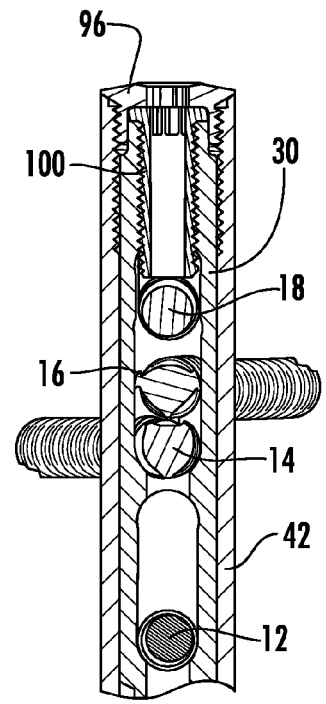
FIG. 7          FIG. 8

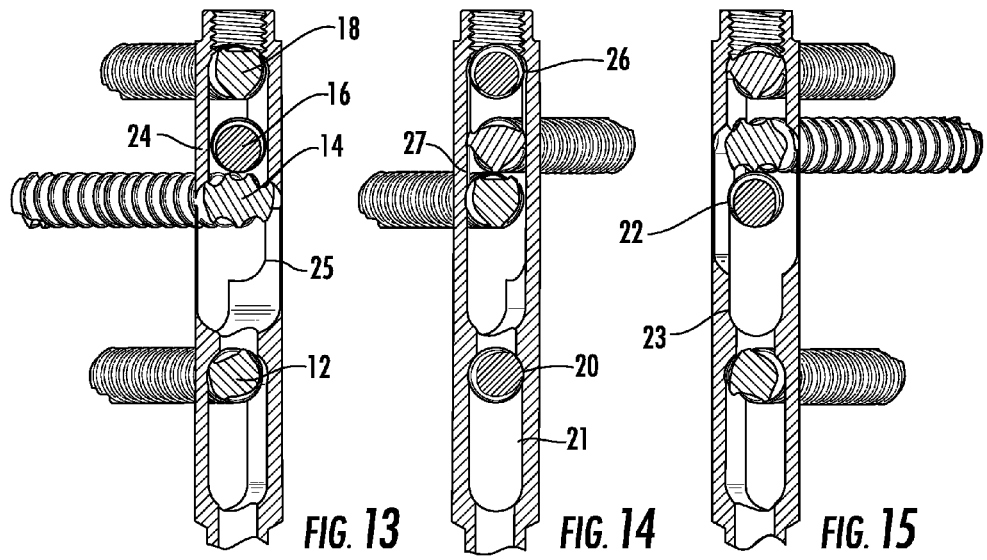
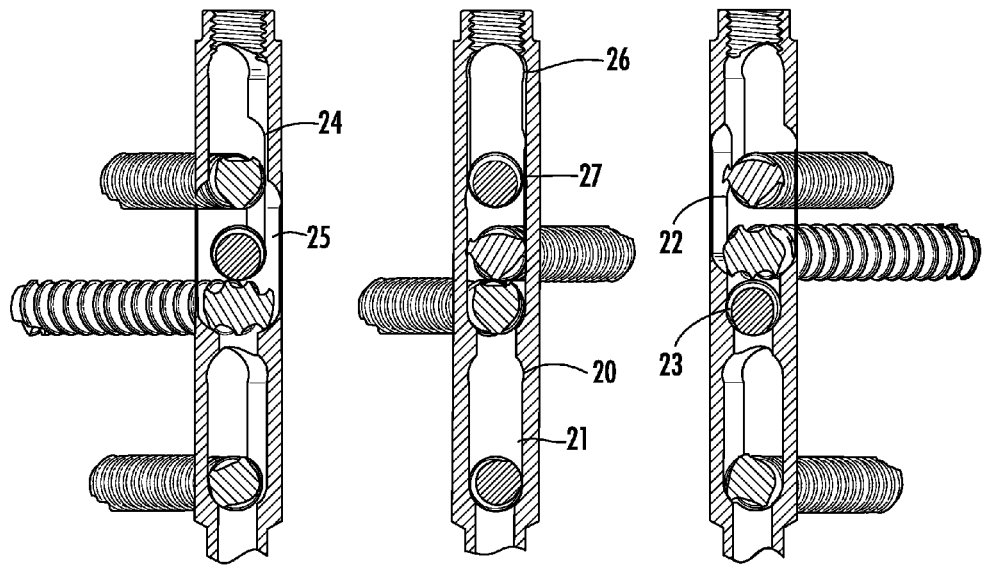

INTRAMEDULLARY NAIL SYSTEM WITH TANG FIXATION AFTER LOCK SCREW PLACEMENT

CROSS-REFERENCE TO RELATED APPLICATION

The application is a continuation-in-part of U.S. application Ser. No. 13/445,954 for Intramedullary Nail System with Tang Fixation filed Apr. 13, 2012.

FIELD

The present invention relates to an intramedullary system for coupling a first and second portion of bone across a fracture.

BACKGROUND

Intramedullary nails were first used in the 1930s. These early nails were inserted into the intramedullary canal of the bone. The result was immediate fixation of fractures, reduction in patient recovery time, increased mobility, and improved quality of life. Multiple examples of such nails are present in the prior art.

But rotation of the inserted nails was a problem. Rotation would result in the nail being in a position different than that chosen by the surgeon. To address this issue, screws were installed that held plates against the outer surface of the bone, used to fix the rotational position of the bone. The plates changed the profile of the bone, potentially causing irritation to surrounding tissue.

The most significant problem caused by the requirement of additional screws is the additional time required under exposure to x-ray radiation. The installation of each screw requires additional x-rays to verify location, depth, and so forth. X-ray radiation is damaging to the patient, but is especially troublesome to the surgeon because each surgeon must perform many of these surgeries. Thus, any reduction in x-rays is highly beneficial.

SUMMARY

The disclosed device solves the problem of fixation of a fractured humerus, or other long bone, by allowing a surgeon to first fix the proximal end of the implant and set the fracture, followed by fixation of the distal end without the use of screws.

The humeral nail solves practical problems encountered during surgery to correct a fracture of the humerus. The two particular problems are: 1) the proximity of nerves to the distal portion of the humerus, near the elbow, and 2) the need to affix the implant on the proximal end, near the shoulder, before affixing the implant on the distal end, near the elbow.

Put simply, the humeral nail is implanted through a penetration in the proximal end of the humerus, passing through one or more fracture lines. It is affixed to the bone on the proximal end by screws, and the distal end by extending tangs, or anchors, that interface with the internal surface of the humerus.

The use of tangs avoids the first problem of damage to nerves in close proximity to the surface of the distal portion of the humerus, avoiding the need for distal screws. By affixing the humeral nail to the interior of the humerus, there is no worry of distally installed screws damaging nerves.

The second problem requires further explanation. When the humerus is fractured it is common for the now-separate pieces of bone to become displaced and misaligned. These separate pieces must be restored to their original positions. This process is known as "reduction."

The surgeon must perform the reduction in conjunction with positioning of the humeral nail because the orientation of the locking screws is important, as is the depth of humeral nail placement. A humeral nail that is too depressed, or placed too deeply within the humerus, may result in locking screw penetrations that are misplaced. A humeral nail that is too prominent, or protruding beyond the head of the humerus, may result in soft tissue damage.

And thus is the problem. The distal tangs must be extended after the locking screws are installed, but the locking screws cross the center of the humeral nail and take up space in the hollow interior cavity of the humeral nail, making access to the distal tangs difficult. The solution is a mechanism that surrounds the installed locking screws, allowing actuation of the distal tangs from the proximal end. As an added benefit, the mechanism acts to secure the locking screws in place, preventing any unscrewing. If upward extending tangs are used, the actuation of the tangs also compresses the fracture. This compression strengthens the bone to allow use of the arm, and encourages healing by minimizing the amount of required bone growth.

Description of the surgical technique is useful to understand many of the unique features present in the disclosed device. The technique described below will be directed at implantation into a human humerus, but a similar technique is employed for other uses.

First, the patient needs to be positioned. The patient is placed in a semi-recumbent "beach chair" position on a radiolucent table. The affected arm is secured to an adjustable side table or arm rest. This position provides a clear view for radiography of the affected arm. The head of the humerus can now be exposed.

An anterolateral approach is performed by starting an incision at the anterolateral tip of the acromion and extending the incision distally over the deltoid muscle. The deltoid muscle is split along its fibers and retracted to expose the supraspinatus muscle and tendon. The supraspinatus tendon is incised in line with its fibers.

Next, the starting point for implantation needs to be determined. The entry point is located at the apex of the humeral head, in line with the medullary canal, or marrow cavity.

Next, an awl or trocar tip guide wire is used to create a hole in the humerus. The location and trajectory are confirmed radiographically using at least two orthogonal images. If a guide wire is used to gain entry into the humerus, a cannulated drill connected to a power driver is passed over the wire and through a tissue protection sleeve. The drill is used to enlarge the hole and allow passage of the implant.

Next, the trocar tip guide wire is exchanged for a ball tip guide wire by way of a flexible exchange tube. If the awl was used to gain entry in the humerus, the ball tip guide wire is passed through its cannulation and down the medullary canal. A ball tip guide wire is necessary for reaming, or enlarging, the medullary canal to accommodate the implant.

Prior to reaming, the humeral nail length must be determined. To provide support the humeral nail must pass the fracture line. Additionally, the distal end of the humeral nail, where the nail tangs are located, must be placed in an area of bone that will allow extension of the nail tangs into the cortex, or dense shell, of the bone. To determine the appropriate humeral nail length, a metal guide, which is visible on an x-ray image, is held over the bone to compare the bone width to the required width shown by the metal guide. The metal guide in combination with a guide wire ruler is used to determine the ideal humeral nail length.

Next, a flexible reamer is passed over the guide wire, enlarging the diameter of the medullary canal to accommodate the distal portion of the humeral nail. After the canal has been reamed to the appropriate diameter, the ball tip guide wire is exchanged for a smooth guide wire.

Next, the nail is slid over the guide wire and inserted into the humeral canal. Insertion can be aided by gentle twisting, constant pressure, or striking with a slap hammer. The guide wire is removed once the humeral nail in fully inserted.

Next, the appropriate version, or rotational alignment, of the humeral nail must be set. This is done using the guide arm, with the patient's forearm serving as a reference. After the version is set, the nail is in its final position.

Next, the proximal locking screws are positioned. Using the guide assembly, a tissue protection sleeve and internal drill sleeve are inserted through an incision in the skin and advanced to the level of the bone. The drill is used to create a hole into the humeral head until the subchondral bone is reached. A measurement is taken from the head of the drill to determine the length of the screw needed at that position. The drill and drill sleeve are removed and the corresponding screw is inserted. This step is repeated for the remaining screw holes, as dictated by the fracture pattern.

Next, the nail tangs are extended. A deployment driver is inserted into the proximal end of the nail, threading into the linear tang actuator. The nail deployment driver is rotated, in turn rotating the actuation screw. The interaction of the first and second actuation threads causes the linear actuator to move axially with respect to the actuator screw.

This in turn causes the tips of the nail tangs to extend beyond the nail portals. The nail tangs will begin to extend through the spongy cancellous bone. The surgeon must monitor the force, taking care to stop the extension of the tangs when the resistance increases sharply, indicating contact with dense cortical bone. Alternatively, the appropriate extension is determined using a torque limiter in conjunction with the nail deployment driver. Ceasing extension of the tangs prior to full deployment is permissible because full deployment is not necessary to affix the nail to the bone.

Finally, the tools used for installation can be removed, and the proximal nail end cap installed to prevent tissue growth over the proximal end of the nail. While the nail is suited for permanent installation, if needed, the procedure is fully reversible. The nail tangs can be retracted and all parts removed.

BRIEF DESCRIPTION OF THE DRAWINGS

The invention can be best understood by those having ordinary skill in the art by reference to the following detailed description when considered in conjunction with the accompanying drawings in which:

FIG. 1 illustrates a first view of a first embodiment of the humeral nail.

FIG. 2 illustrates a second view of a first embodiment of the humeral nail.

FIG. 5 illustrates a first view of the proximal portion of the humeral nail in a non-actuated position.

FIG. 6 illustrates a second view of the proximal portion of the humeral nail in a non-actuated position.

FIG. 7 illustrates a first view of the proximal portion of the humeral nail in an actuated position.

FIG. 8 illustrates a second view of the proximal portion of the humeral nail in an actuated position.

FIG. 13 illustrates an interior, cross-sectional view of a first embodiment of the humeral nail in a non-actuated position.

FIG. 14 illustrates a second interior, cross-sectional view of a first embodiment of the humeral nail in a non-actuated position.

FIG. 15 illustrates a third interior, cross-sectional view of a first embodiment of the humeral nail in a non-actuated position.

FIG. 16 illustrates an interior, cross-sectional view of a first embodiment of the humeral nail in an actuated position.

FIG. 17 illustrates a second interior, cross-sectional view of a first embodiment of the humeral nail in an actuated position.

FIG. 18 illustrates a third interior, cross-sectional view of a first embodiment of the humeral nail in an actuated position.

DETAILED DESCRIPTION

Figure 3:
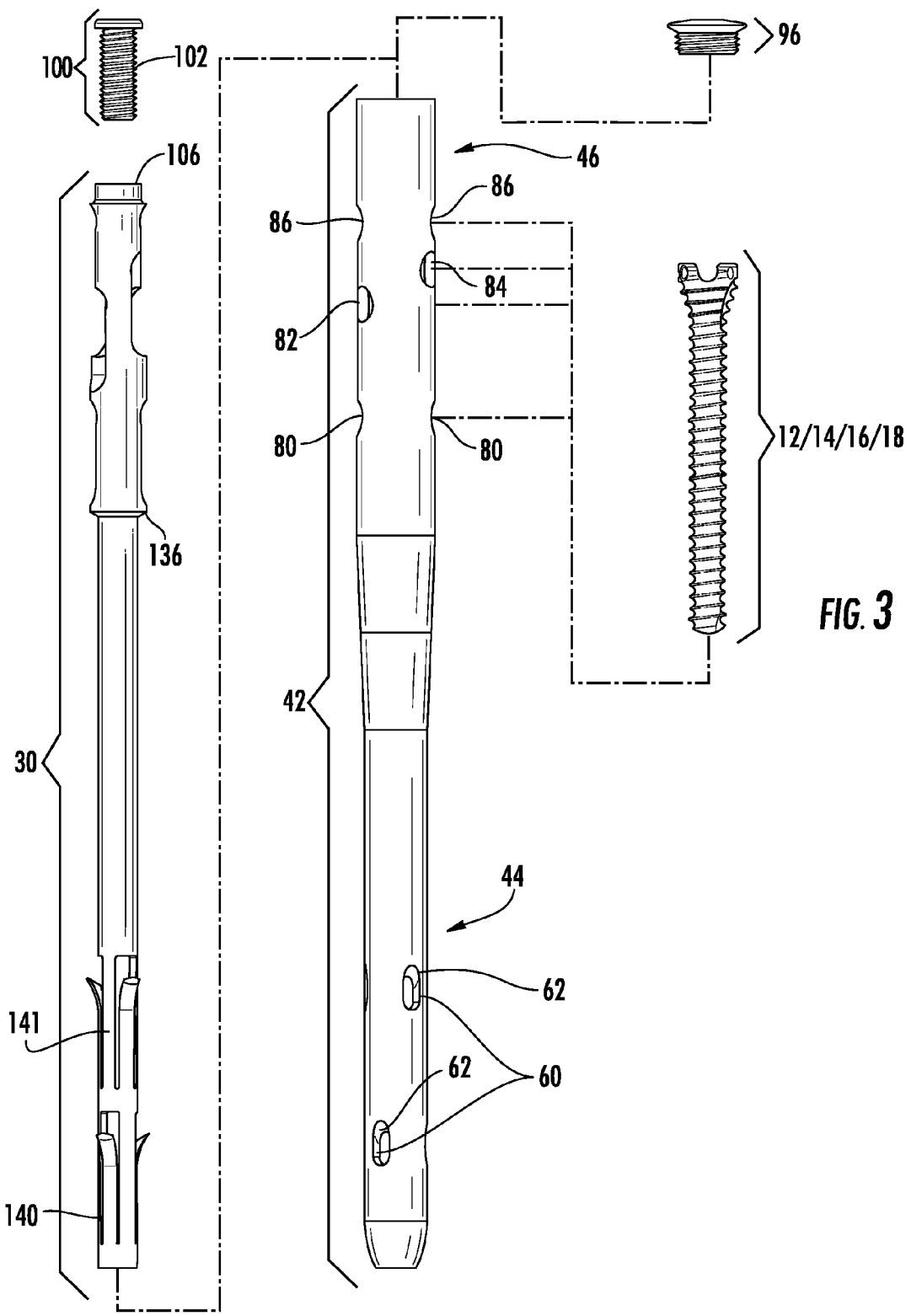
FIG. 3 illustrates an exploded view a first embodiment of the humeral nail.

Reference will now be made in detail to the presently preferred embodiments of the invention, examples of which are illustrated in the accompanying drawings. Throughout the following detailed description, the same reference numerals refer to the same elements in all figures.

Referring to FIGS. 1-2, the humeral nail 40 is shown. The humeral nail 40 is shown inserted into the intramedullary canal 10 of the humerus 2, the humerus having a proximal portion 4. An exemplary fracture line 6 is shown, the fracture line 6 representing a surgical neck fracture. Other types of fractures that can be treated using the humeral nail 40 include fractures of the anatomical neck and fractures of the greater tuberosity.

The humeral nail is adaptable to work in any long bone, the tibia being one such example.

Locking screws 12, 14, 16, and 18 are shown. The number of screws used and the choice of which screws is made by the surgeon.

Upper nail tangs 141 and lower nail tangs 140 are shown in their fully extended position.

Figure 4:
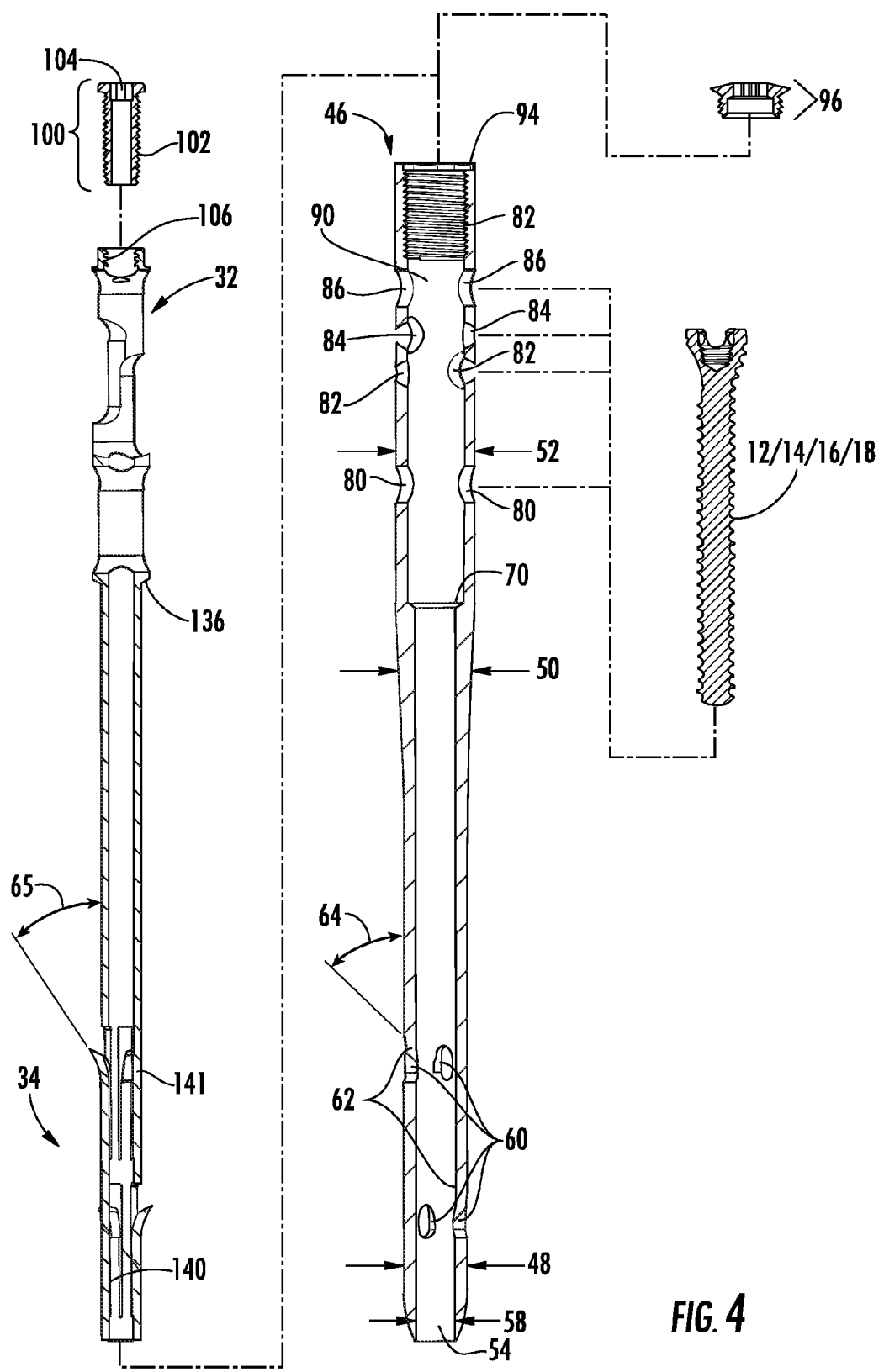
FIG. 4 illustrates a cross-sectional and exploded view of a first embodiment of the humeral nail.
Figures 9, 10:
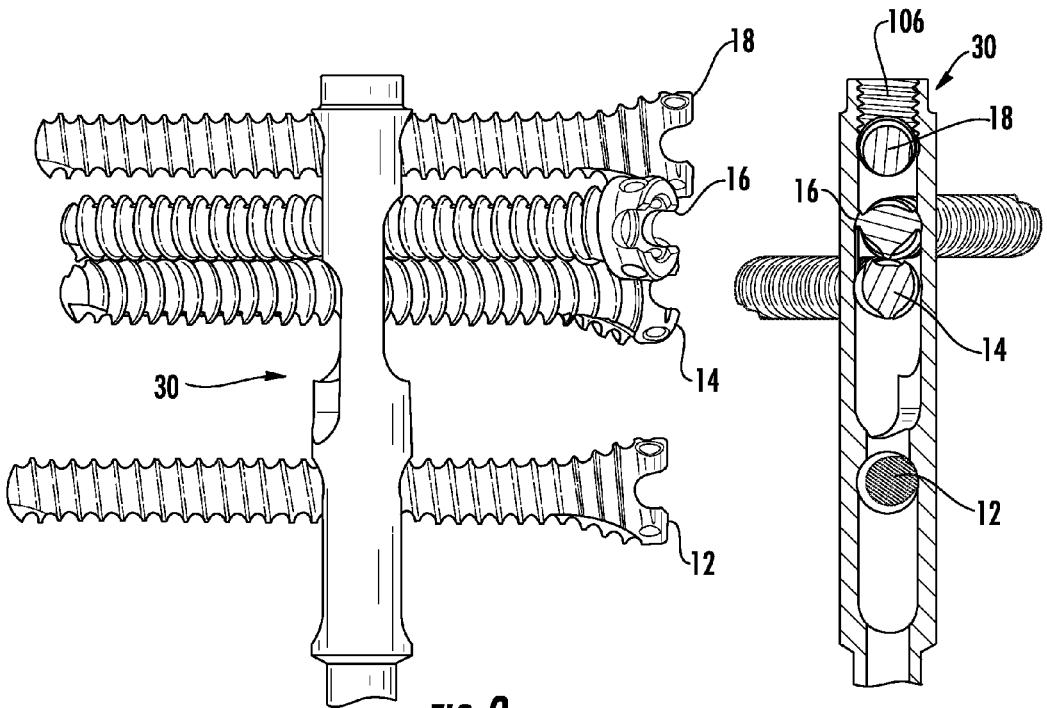
FIG. 9 illustrates a first interior view of the linear tang actuator portion of the humeral nail in a non-actuated position.
FIG. 10 illustrates a second interior, cross-sectional view of the linear tang actuator portion of the humeral nail in a non-actuated position.
Figures 11, 12:
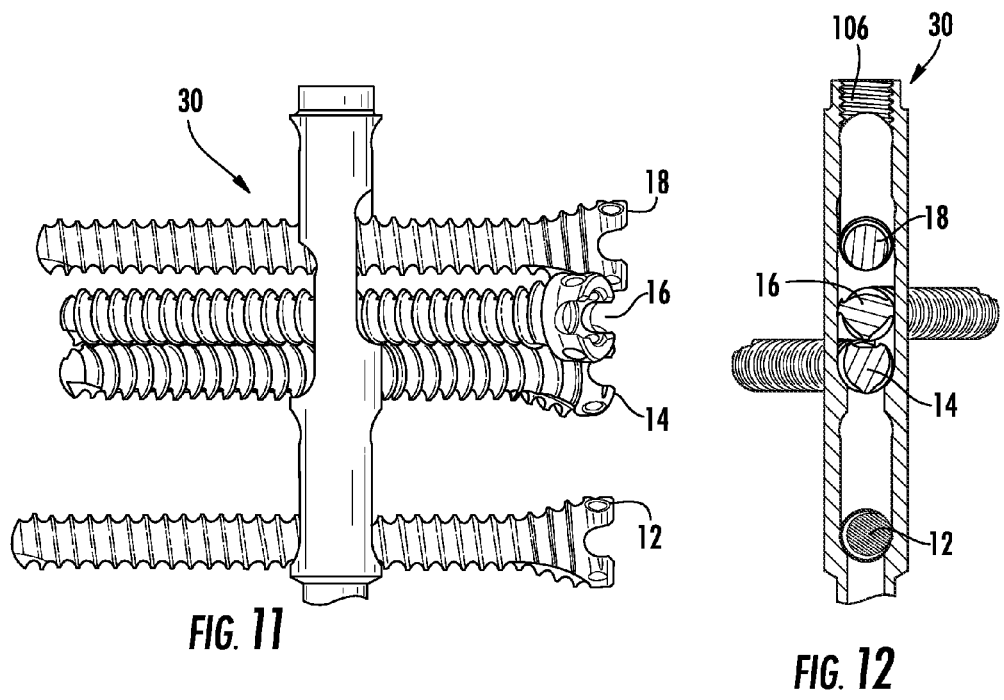
FIG. 11 illustrates a first interior view of the linear tang actuator portion of the humeral nail in an actuated position.
FIG. 12 illustrates a second interior, cross-sectional view of the linear tang actuator portion of the humeral nail in an actuated position.

Referring to FIGS. 3-4, the humeral nail 40, with its internal components, is further described.

This embodiment of the humeral nail 40 is cylindrical in cross-section, and straight along its length, but neither shape is a requirement. Alternative cross-sections such as square, hex shaped, or lobular, allow for linear motion of internal components while fixing rotational position. Alternative shapes along its length are also acceptable, likely chosen to mimic the shape of the bone into which the nail must fit.

The two primary components of the humeral nail 40 are the nail body 42 and the linear tang actuator 30. The nail body 42 includes a distal portion 44 and a proximal portion 46. The nail body 42 has a nail body distal outside diameter 48, a nail body transitional diameter 50, and a nail body proximal outside diameter 52. The distal portion 44 of nail body 42 has a nail distal end bore 54 with nail distal bore diameter 58.

The distal portion 44 of the nail body 42 has a rounded tip to ease insertion into the intramedullary canal 10 (not shown). Other tapered shapes are also acceptable, including a chamfered tip.

The upper tangs 141 and lower tangs 140 have pre-curved tips 150. The pre-curved tips 150 have nail tang slant angle 65.

The upper tangs 141 and lower tangs 140 pass through nail tang portals 60 present in the nail body 42. The presence of multiple sets of tangs creates additional fixation, but one set of tangs is acceptable. As the tangs pass through the nail tang portals 60 they slide against the nail portal slanted surfaces 62, which each have a nail portal slant angle 64 relative to the longitudinal axis of the nail body 42. The result, as shown in later figures, is bending of the nail tangs 140/141, resulting in curved nail tangs 140/141.

During assembly, the linear tang actuator 30 is inserted into the nail body 42 until the linear tang actuator rest surface 136 rests against the nail body rest surface 70. The linear tang actuator 30 is shown as a single piece, but could be constructed of multiple pieces. Such multiple pieces could be fused together, affixed mechanically, or be able to move with respect to one another.

Turning to fixation of the proximal end of the humeral nail 40, each lock screw 12/14/16/18 has corresponding lock screw portals 80/82/84/86. First locking screw 12 is inserted through first lock screw portals 80. Second locking screw 14 is inserted through second lock screw portals 82. Third locking screw 16 is inserted through third lock screw portals 84. And fourth locking screw 18 is inserted through fourth lock screw portals 86.

The proximal portion 46 of the nail body 42 includes numerous features that provide for interaction between the nail body 42 and linear tang actuator 30. The nail proximal bore 90 is the inner bore within the proximal end of the nail body 46, through which the linear tang actuator 30 passes during assembly of the humeral nail 40. A portion of the nail proximal bore 90 is threaded, creating the nail proximal threads 92.

As discussed above, the linear tang actuator 30 is moved through use of actuation screw 100. The first actuation threads 102 of the actuation screw 100 mate with the second actuation threads 106 of the linear tang actuator 30. Rotation is performede using a tool (not shown) that interfaces with the actuation head 104 of the actuation screw 100.

Following actuation, the proximal portion 46 of nail body 42 is covered by the nail end cap 96, which interfaces with the nail proximal threads 92, resting against the nail end cap seat 94.

Referring to FIGS. 5-8, pre and post actuation views of the linear tang actuation are shown. As discussed above, the humeral nail allows for actuation of the nail tangs 140/141 after the locking screws 12/14/16/18. One embodiment of a mechanism that allows for this actuation is shown in the figures. The linear tang actuator 30 is shaped to move around the locking screws, allowing for the axial force to be transferred from the actuation screw 100 at the top of the humeral nail 40 to the tangs 140/141 at the bottom of the nail. The linear tang actuator 30 passes around the locking screws 12/14/16/18, transmitting the force from the actuation screw 100 to the tangs 140/141; bridging the two ends of the humeral nail 40 to move the force around the locking screws 12/14/16/18.

FIG. 5 shows a partial-sectional side view of the locking screws 12/14/16/18 interacting with the linear tang actuator 30 prior to actuation.

FIG. 6 shows a cross-sectional view of the locking screws 12/14/16/18 and linear tang actuator 30, prior to actuation.

FIG. 7 shows a partial-sectional side view of the locking screws 12/14/16/18 interaction with the linear tang actuator 30 after complete actuation.

FIG. 8 shows a cross-sectional view of the locking screws 12/14/16/18 and linear tang actuator 30, after complete actuation.

FIGS. 5-6 show the relationship of the linear tang actuator 30, locking screws 12/14/16/18, and actuation screw 100 prior to actuation of the mechanism, and thus before extension of the tangs 140/141 (not shown). The actuation screw 100 is braced against the fourth locking screw 18. The first actuation threads 102 of the actuation screw 100 are threaded into the second actuation threads 106 of the linear tang actuator 30. As the actuation screw 100 is turned, the interaction of the threads 102/106 draws the linear tang actuator 30 upwards. The result is a reduction in the distance between the proximal end 32 of the linear tang actuator 30 and the proximal end 46 of the nail body 42, pulling the linear tang actuator 30 upwards. The upward force of the first actuation threads 102 against the second actuation threads 106 is countered by a downward force by the actuation screw 100 against the fourth locking screw 18.

Nail end cap 96 is cannulated, or has a central penetration, which is useful for nail removal. When the actuation screw 100 is turned in a reverse direction, rather than bracing against the fourth lock screw 18 the actuation screw 100 braces against the inner portion of the nail end cap 96. This allows the actuation screw 100 to provide a downward force against the linear tang actuator 30.

FIGS. 7-8 show the relationship of the linear tang actuator 30, locking screws 12/14/16/18, and actuation screw 100 after complete actuation of the mechanism, and thus after extension of the tangs 140/141 (not shown). The actuation screw 100 has drawn the linear tang actuator 30 completely upward. The upper portion of the linear tang actuator 30 has filled the space between the actuation screw 100 and the nail end cap 96. While this will be more thoroughly explained in subsequent figures, FIG. 8 shows the movement of the linear tang actuator 30 around the locking screws 12/14/16/18.

Referring to FIG. 9-12, pre and post actuation views of the linear tang actuation are shown with the nail body 42 hidden to show the interaction of the linear tang actuator 42 and the locking screws 12/14/16/18.

Referring to FIG. 13-18, pre and post actuation views of the linear tang actuation are shown, with different views showing the compression action of the keyhole shaped slots.

The linear tang actuator 30 has keyhole-shaped slots for the penetration of locking screws 12/14/16/18. This provides two specific advantages over the prior art. First, the keyhole-shaped slots grip and compress the locking screws 12/14/16/18 after actuation, preventing the screws from backing out. Second, the shape of the slots allows for the reduction process to be completed and locking screws 12/14/16/18 to be installed before tang 140/141 extension.

Comparison of the figures shows that the screws are non-co-planar. If the axis of each locking screw 12/14/16/18 is viewed as lying within a plane, locking screw 12 does not share a plane with locking screw 14, nor locking screw 12 with locking screw 16. In this embodiment, locking screw 12 and locking screw 18 share a plane, but in other embodiments these locking screws 12/18 do not. The result is that the keyhole-shaped slots within the linear tang actuator are non-co-planar.

The linear tang actuator 30 allows for the transmission of force around a multiplicity of non-co-planar locking screws 12/14/16/18, each non-co-planar locking screw 12/14/16/18 penetrating the linear tang actuator 30 through its own slot, the result being that each slot is non-co-planar.

Each locking screw has an associated keyhole-shaped slot. Each slot has a larger upper, or proximal, portion where the locking screw 12/14/16/18 is inserted during reduction. The slot immediately narrows, and as a result the rising motion of the linear actuator brings the narrower portion of the keyhole shaped slots to bear on each respective locking screw 12/14/16/18, squeezing the screw and holding it in place. This squeezing force prevents the screws from backing out. Because the extension of the tangs 140/141 can be stopped at any point the surgeon deems appropriate, it is helpful that the locking screws 12/14/16/18 become fixed as soon as the tangs 140/141 begin extension. The squeezing force then remains continuous throughout the remaining travel of the linear tang actuator 30.

The first locking screw 12 has a first locking screw broad gap 20 and a first locking screw narrow gap 21. The second locking screw 14 has a second locking screw broad gap 22 and a second locking screw narrow gap 23. The third locking screw 16 has a third locking screw broad gap 24 and a third locking screw narrow gap 25. The fourth locking screw 18 has fourth locking screw broad gap 26 and a fourth locking screw narrow gap 27. Each combination of a broad gap and a narrow gap results in a keyhole-shaped slot.

Alternative means of drawing the linear tang actuator 30 upwards exist. Examples included a tool that draws the linear tang actuator 30 upward much like the actuation screw 100, but braces against the nail body 42, or other external surface, rather than the fourth locking screw 18. The benefit of this arrangement is that the fourth locking screw 18 is no longer required. This tool would interface with the second actuation threads 106 of the linear tang actuator 30 to draw the linear tang actuator 30 upwards.

Alternatively, a linear ratchet tool could be used. Such a tool would also brace itself against the nail body 42 or other external surface, but would not draw the linear tang actuator 30 upwards by rotating a screw within the second actuation threads 106, but instead by a linear (non-rotational) ratcheting action. The linear ratchet tool would draw the linear tang actuator 30 upwards an incremental amount, reset, and repeat. When the upward amount was correct the linear ratchet tool would be removed, and a modified cap screw installed that threaded into the second actuation threads 106 and interfaced with the nail end cap seat 94 to prevent the linear tang actuator 30 from moving downward.

Figure 19:
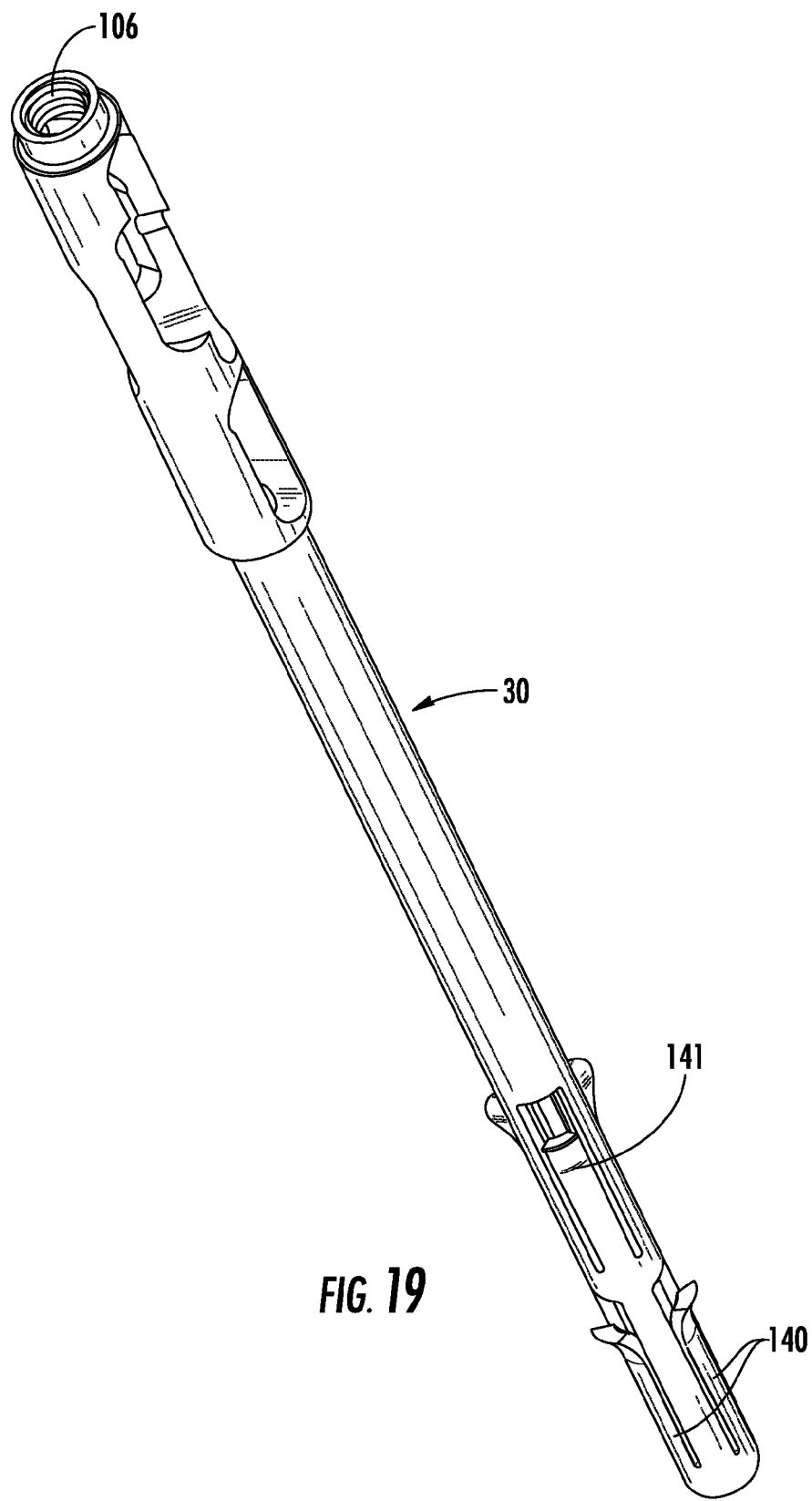
FIG. 19 illustrates an isometric view of a first embodiment of the linear tang actuator of the humeral nail.

Referring to FIG. 19, an isometric view of the linear tang actuator 30 is shown.

Figure 20:
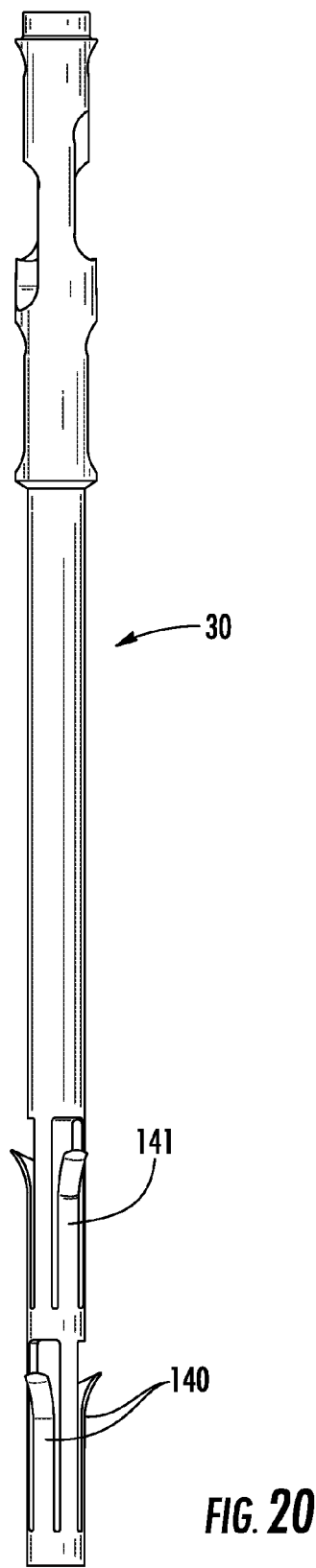
FIG. 20 illustrates a front view of a first embodiment of the linear tang actuator of the humeral nail.

Referring to FIG. 20, a front view of the linear tang actuator 30 is shown.

Figure 21:
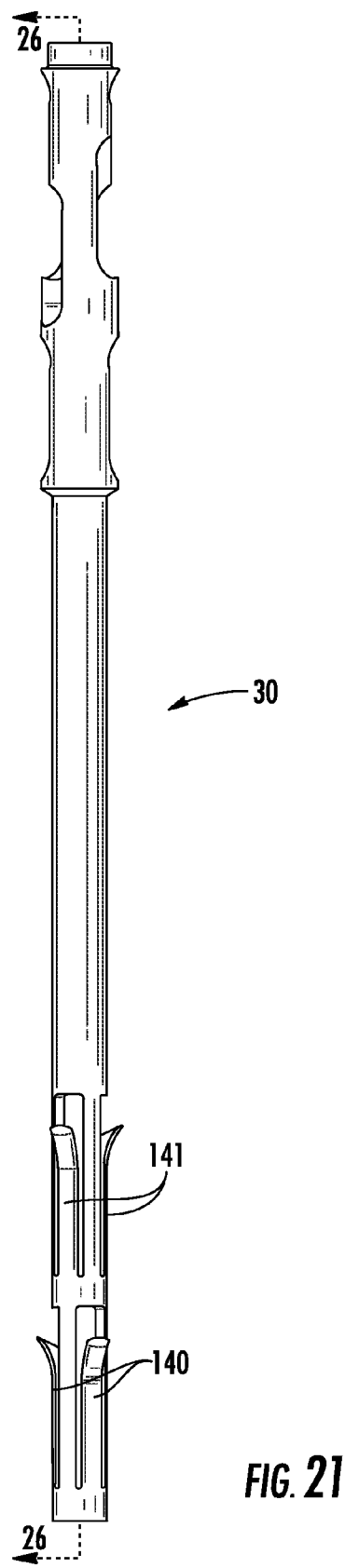
FIG. 21 illustrates a back view of a first embodiment of the linear tang actuator of the humeral nail.

Referring to FIG. 21, a back view of the linear tang actuator 30 is shown.

Figure 22:
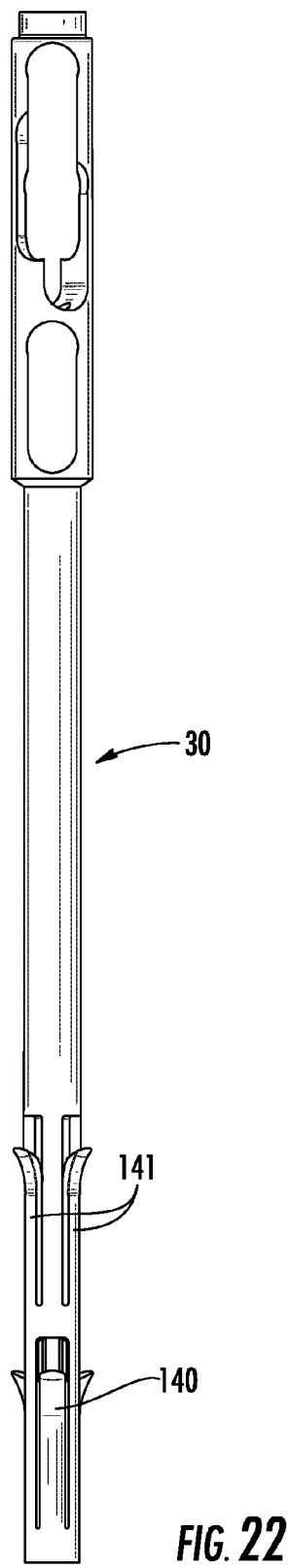
FIG. 22 illustrates a right view of a first embodiment of the linear tang actuator of the humeral nail.

Referring to FIG. 22, a right view of the linear tang actuator 30 is shown.

Figure 23:
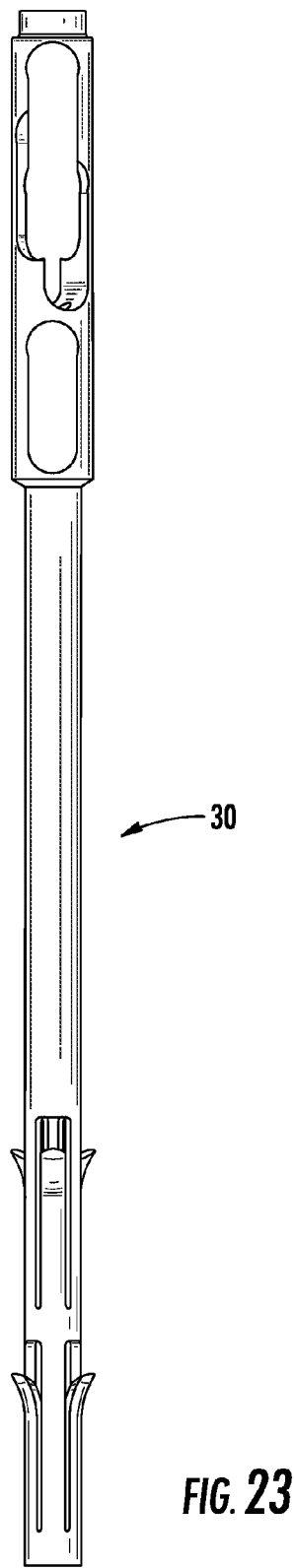
FIG. 23 illustrates a left view of a first embodiment of the linear tang actuator of the humeral nail.

Referring to FIG. 23, a left view of the linear tang actuator 30 is shown.

Figure 24:
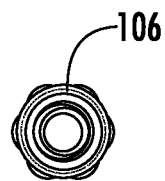
FIG. 24 illustrates a top view of a first embodiment of the linear tang actuator of the humeral nail.

Referring to FIG. 24, a top view of the linear tang actuator 30 is shown.

Figure 25:
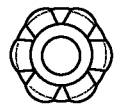
FIG. 25 illustrates a bottom view of a first embodiment of the linear tang actuator of the humeral nail.

Referring to FIG. 25, a bottom view of the linear tang actuator 30 is shown.

Figure 26:
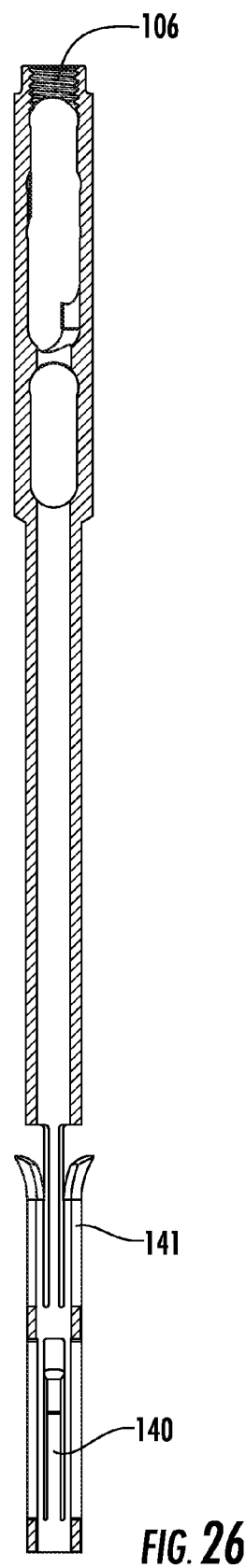
FIG. 26 illustrates a cross-sectional view of a first embodiment of the linear tang actuator of the humeral nail.

Referring to FIG. 26, a cross-sectional view of the linear tang actuator 30 is shown.

Figure 27:
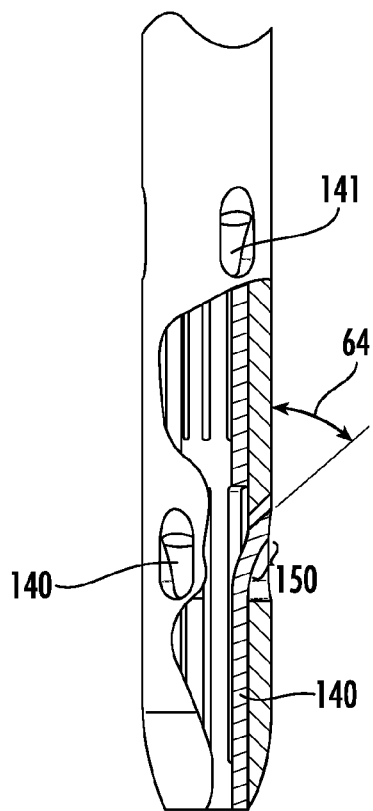
FIG. 27 illustrates a partial-cross-sectional view of the distal portion of a first embodiment of the humeral nail in a non-actuated position.
Figure 28:
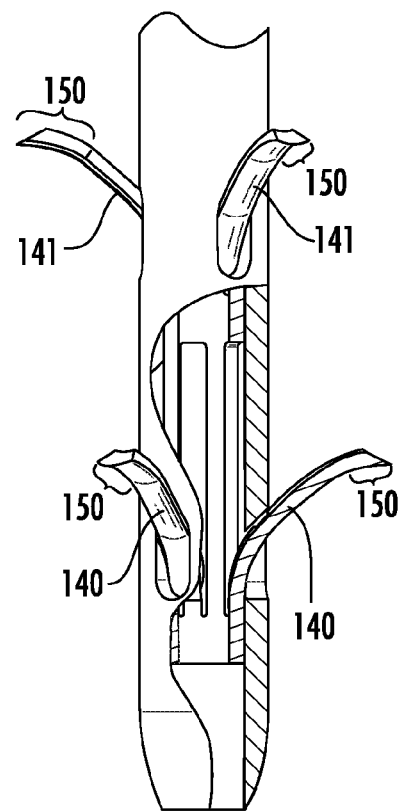
FIG. 28 illustrates a partial-cross-sectional view of the distal portion of a first embodiment of the humeral nail in an actuated position.

Referring to FIG. 27-28, the operation of the tangs is shown. The tangs 140/141 include pre-curved tips 150. The shape of the nail tang pre-curved tips 150 performs a number of functions: First, the tangs 140/141 extend in the upward direction, toward the proximal portion 46 of the nail 40. Because the proximal portion 46 of the nail 40 is affixed to the humerus 2 before the tangs are extended, the proximal portion 46 of the nail 40 is fixed. The upward motion of the tangs 140/141 pulls the distal portion 44 of the nail 40 downward, correspondingly pushing the distal portion of the humerus 2 upward. The result is compression of the fracture line 6. This compressive action stabilizes the bone, allowing the patient to use the arm sooner in the recovery process. Closing the gap minimizes the amount of bone the body must regenerate, and thus reduces the time required for full recovery.

There is no requirement that the surgeon extend the tangs a specific amount.

Second, during assembly, when the nail tangs 140/141 are moved into place in the distal portion of the nail body, the nail tang pre-curved tips 150 of the opposing nail tangs 140/141 snap, or pop, into their respective nail portals 60. The selflocating feature of the nail tangs 140/141 with the nail tang pre-curved tips 150 simplifies assembly, and ensures that the tangs are properly located.

Third, in this installed position, the nail tang pre-curved tips 150 rest against the nail portal slanted surfaces 62. The nail portal slanted surfaces 62 serve to smoothly guide the opposing nail tangs 140/141 through their path to exit the nail body 42. The pre-curved nature of the tips 150 begins the process of plastic deformation of the opposing nail tangs 140/141 as they exit the nail tang portals 60, guided by the nail portal slanted surfaces 62. The angle 64 of the slanted surfaces 62 controls the shape of the opposing nail tangs 140/141 during the process of plastic deformation. Much as a die is used to create an extruded shape during extrusion, the shape of the nail portal 60 and angle 64 of the nail portal slanted surface 62 serves to shape each opposing nail tang 140/141 as it passes through.

Fourth, the shape of the nail tang pre-curved tips 150 shape allows the opposing nail tangs 140/141 to be present in the nail tang portals prior to extension. This allows the opposing nail tangs 140/141 to almost immediately contact the interior surface of the bone. The result is a reduction in surgery time and fewer turns required prior to contact. As a result, the humeral nail 40 is less likely to rotate out of place during actuation.

Figure 29:
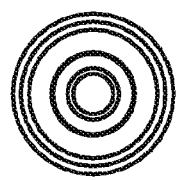
FIG. 29 illustrates a bottom view of a first embodiment of the humeral nail in a non-actuated position.

Referring to FIG. 29, a bottom view of the humeral nail 40 is shown. The humeral nail 40 is in the non-actuated position, thus the tangs 140/141 are not visible.

Figure 30:
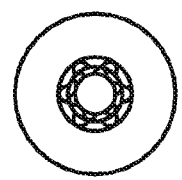
FIG. 30 illustrates a top view of a first embodiment of the humeral nail in a non-actuated position.

Referring to FIG. 30, a top view of the humeral nail 40 is shown. The humeral nail 40 is in the non-actuated position, thus the tangs 140/141 are not visible.

Figure 31:
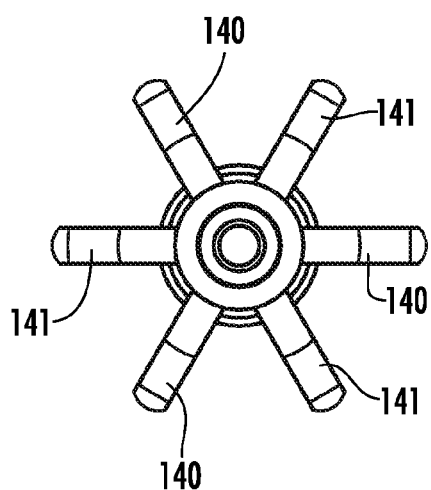
FIG. 31 illustrates a bottom view of a first embodiment of the humeral nail in an actuated position.

Referring to FIG. 31, a bottom view of the humeral nail 40 is shown. The humeral nail 40 is in the actuated position, thus the tangs 140/141 are visible. It can be seen that in this embodiment the upper tangs 141 and lower tangs 140 are offset by sixty degrees.

Figure 32:
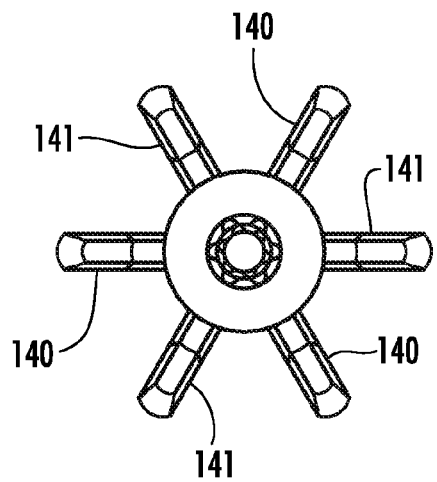
FIG. 32 illustrates a top view of a first embodiment of the humeral nail in an actuated position.

Referring to FIG. 32, a top view of the humeral nail 40 is shown. The humeral nail 40 is in the actuated position, thus the tangs 140/141 are visible.

Figure 33:
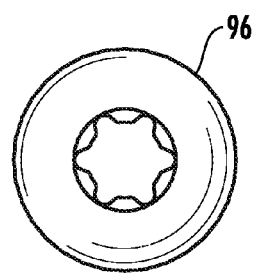
FIG. 33 illustrates a top view of a first embodiment of the nail end cap.
Figure 34:
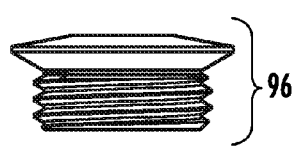
FIG. 34 illustrates a side view of a first embodiment of the nail end cap.
Figure 35:
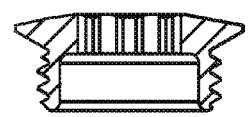
FIG. 35 illustrates a cross-sectional view of a first embodiment of the nail end cap.

Referring to FIGS. 33-35, the nail end cap 96 is shown. The nail end cap 96 is shown with a Torx type interface, but any interface is acceptable.

Figure 36:
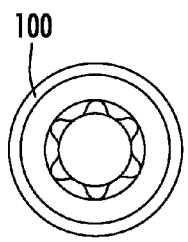
FIG. 36 illustrates a top view of a first embodiment of the actuation screw.
Figure 37:
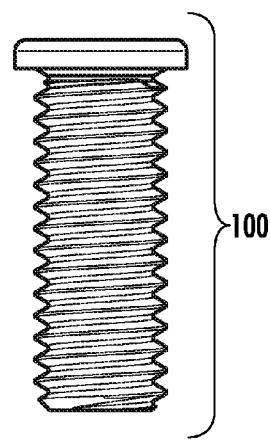
FIG. 37 illustrates a side view of a first embodiment of the actuation screw.
Figure 38:
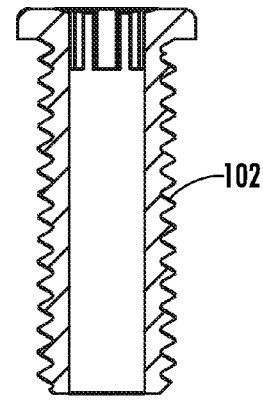
FIG. 38 illustrates a cross-sectional view of a first embodiment of the actuation screw.

Referring to FIG. 36-38, the actuation screw 100 is shown. The actuation screw 100 is shown with a Torx type interface, but any interface is acceptable.

Figure 39:
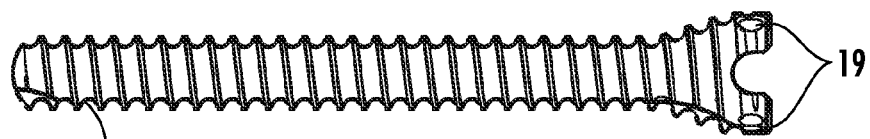
FIG. 39 illustrates a first view of a first embodiment of the locking screw.
Figure 40:
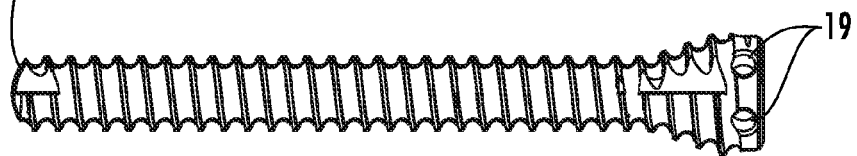
FIG. 40 illustrates a second view of a first embodiment of the locking screw.

Referring to FIG. 39-40, the locking screw 12/14/16/18 is shown. Optional locking screw 12/14/16/18 features include self-tapping, where the screw creates its own thread (shown); and self-drilling, where the screw creates its own hole, in addition to self-tapping.

The suture holes 19 can be used as anchor points for surgical sutures. Sutures may be used during surgery for fixation of the lesser tuberosity, or suturing the rotator cuff.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An orthopedic bone implant to mend a fracture of a humerus through distal and proximal bone fixation, proximal bone fixation using one or more locking screws, distal bone fixation using three or more extendable nail tangs, the three or more extendable nail tangs actuated using a linear tang actuator that passes around the one or more locking screws, allowing linear movement of the linear tang actuator after installation of the one or more locking screws.

2. The orthopedic bone implant of claim 1, wherein the orthopedic bone implant is sized and shaped for implantation within an intramedullary canal of a human humerus.

3. The orthopedic bone implant of claim 1, wherein the distal bone fixation using the three or more extendable tangs further prevents the one or more locking screws from unthreading.

4. The orthopedic bone implant of claim 1, wherein actuation of the linear tang actuator causes one or more keyhole-shaped slots to move with respect to the one or more locking screws, the movement of the one or more keyhole-shaped slots causing compression between one of the one or more keyhole-shaped slots and its respective locking screw of the one or more locking screws, the result being that the locking screw of the one or more locking screws is held within the orthopedic bone implant.

5. The orthopedic bone implant of claim 4, wherein the three or more extendable nail tangs has a pre-curved tip, the pre-curved tip being offset at an angle with respect to the remainder of its associated extendable nail tang.

6. The orthopedic bone implant of claim 1, the orthopedic bone implant having a proximal end and a distal end, wherein actuation of the linear tang actuator is achieved through use of an actuation screw, the actuation screw bracing itself against the locking screw of the one or more locking screws that is closest to the proximal end, the actuation screw interacting with the linear tang actuator such that rotation of the actuation screw causes the linear tang actuator to move toward the proximal end of the orthopedic bone implant.

7. The orthopedic bone implant of claim 1, further comprising:
   a. a nail body having a proximal end and a distal end;
   b. one or more locking screws penetrating the nail body near its proximal end;
   c. the three or more extendable nail tangs being located near the distal end of the nail body; and
   d. an internal mechanism for actuation of the three or more extendable nail tangs after installation of the one or more locking screws, wherein the internal mechanism allows for actuation of the three or more extendable nail tangs from the proximal end of the nail body after installation of the one or more locking screws.

8. An apparatus for affixing an orthopedic implant within a proximal portion of a humerus before affixing to a distal portion within a humerus, the apparatus comprising:
   a. an implantable nail with proximal and distal ends;
   b. the implantable nail including deployable tangs near the distal end of the implantable nail;
   c. two or more non-co-planar locking screws, wherein the two or more non-co-planar locking screws remain after implantation of the apparatus; and
   d. the deployable tangs able to be actuated from the proximal end of the nail after installation of two or more non-co-planar locking screws.

9. The apparatus for affixing an orthopedic implant within a proximal portion of a humerus before affixing to a distal portion within a humerus of claim 8, the apparatus further comprising:

a. a linear tang actuator including a proximal end and a distal end;
b. the linear tang actuator internal to the implantable nail;
c. the linear tang actuator interfaced with two or more deployable tangs; and
d. the linear tang actuator bridging the two or more deployable tangs and the proximal end of the implantable nail.

10. The apparatus for affixing an orthopedic implant within a proximal portion of a humerus before affixing to a distal portion within a humerus of claim 9, the apparatus further comprising:
   a. One or more keyhole-shaped slots, the one or more keyhole-shaped slots as part of the linear tang actuator, each of the one or more keyhole-shaped slots associated with the two or more non-co-planar locking screws.

11. The apparatus for affixing an orthopedic implant within a proximal portion of a humerus before affixing to a distal portion within a humerus of claim 10, the apparatus further comprising:
   a. an actuation screw, the actuation screw threaded into the proximal end of the linear tang actuator, such that rotation of the actuation screw causes linear motion of the linear tang actuator.

12. The apparatus for affixing an orthopedic implant within a proximal portion of a humerus before affixing to a distal portion within a humerus of claim 9, the apparatus further comprising:
   a. an actuation screw, the actuation screw threaded into the proximal end of the linear tang actuator, such that rotation of the actuation screw causes linear motion of the linear tang actuator.

13. An apparatus for fixation of a fractured humerus, the apparatus including a linear actuator that distally actuates two or more extendable tangs after proximal installation of two or more non-co-planar locking screws.

14. The apparatus for fixation of a fractured humerus of claim 13, wherein the two or more extendable tangs are curved metal extensions that, when extended, protrude from the apparatus, the two or more extendable tangs affixing the apparatus to an intramedullary canal within a humerus.

15. The apparatus for fixation of a fractured humerus of claim 14:
   a. wherein the apparatus is sized for implantation within the intramedullary canal of a human humerus; and
   b. the non-co-planar locking screws are intended for installation into a head of the human humerus.

16. The apparatus for fixation of a fractured humerus of claim 13, wherein each of the two or more extendable tangs has a first position substantially within the apparatus, and a second position penetrating an outer surface of the apparatus.

* * * * *